United States Patent [19]

Armitage et al.

[11] 3,959,364

[45] May 25, 1976

[54] PREPARATION OF ARYLALKANOIC ACIDS

[75] Inventors: Bernard J. Armitage; James E. Jeffery; John S. Nicholson, all of Beeston; James G. Tantum, Nuthall, all of England

[73] Assignee: The Boots Company Limited, Nottingham, England

[22] Filed: May 20, 1974

[21] Appl. No.: 471,308

[30] Foreign Application Priority Data

May 24, 1973 United Kingdom............... 24844/73

[52] U.S. Cl............................ 260/515 R; 260/243 B; 260/247.2 R; 260/326.47; 260/332.2 A; 260/515 A; 260/516; 260/517; 260/518 R; 260/520 R

[51] Int. Cl.²......................................... C07C 51/00

[58] Field of Search............... 260/515 A, 520, 516, 260/517, 518 R, 518 A, 295 R, 332.2 A

[56] References Cited

UNITED STATES PATENTS

| | | | |
|---|---|---|---|
| 2,290,401 | 7/1942 | Witman | 260/515 |
| 2,921,939 | 1/1960 | Ramsden | 260/295 |
| 3,385,887 | 5/1968 | Nicholson et al. | 260/515 |

*Primary Examiner*—James A. Patten
*Attorney, Agent, or Firm*—Gordon W. Hueschen

[57] ABSTRACT

A novel process for making aryl propionic acids is described. It comprises reaction of a Grignard compound, obtained from an aryl bromide and magnesium, with a lithium, sodium, magnesium or calcium salt of 2-bromopropionic acid, followed by acidification.

20 Claims, No Drawings

PREPARATION OF ARYLALKANOIC ACIDS

This invention relates to therapeutic agents and in particular to a process for preparing therapeutic agents.

It is well known that a large number of 2-arylpropionic acids have valuable therapeutic properties, and many possess, for example, anti-inflammatory activity.

There are many processes for preparing such compounds. Recently it has been proposed to react an aryl magnesium halide with a 2-halopropionic acid or a derivative thereof and in German OLS No. 2145650 the use of potassium 2-iodopropionate has been specifically described.

We have now found that when the lithium, sodium, magnesium or calcium salt of 2-bromopropionic acid is reacted with an aryl magnesium bromide, yields of any particular 2-arylpropionic acid are obtained which are higher than when a reaction is carried out under similar conditions to obtain the same 2-arylpropionic using any other comparable combination of arylmagnesium halide and 2-halopropionic acid or derivative thereof, that we have attempted. In particular yields of over 60% of surprisingly high quality unpurified 2-(2-fluoro-4-biphenylyl)propionic acid have been obtained by coupling sodium 2-bromopropionate with 2-fluoro-4-biphenylylmagnesium bromide. Such high yields are surprising for this type of coupling reaction.

Thus according to the invention there is provided a process for the preparation of a compound of formula I

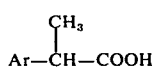

in which Ar is an aryl group which comprises reacting a Grignard compound, obtained from Ar$_1$Br and magnesium, with a lithium, sodium, magnesium or calcium salt of 2-bromopropionic acid, followed by acidification and in which Ar$_1$ is Ar or a group convertible to Ar during acidification.

The Ar group is generally a substituted phenyl group of formula

in which $n$ is an integer of 1 to 4, preferably 1 or 2, and Q is the same or different and is selected from alkyl, e.g. methyl, ethyl, propyl, butyl, (especially isobutyl), pentyl, branched hexyl and heptyl; aralkyl, e.g. benzyl; alkenyl, e.g. allyl and propenyl; cycloalkyl, e.g. of three to seven carbon atoms, and especially cyclohexyl; alkyl substituted cycloalkyl; cycloalkenyl, e.g. cyclohexenyl; aryl, e.g. phenyl and phenyl substituted with, for example 1 or 2 alkyl, alkoxy, or alkylthio, e.g. methylthio, cyano, or halogen groups; alkoxy e.g. methoxy, isopropoxy; aralkoxy e.g. benzyloxy; alkenyloxy, e.g. allyloxy and butenyloxy; cycloalkoxy e.g. cyclohexyloxy; cycloalkenyloxy; aryloxy, e.g. phenoxy and phenoxy substituted with, for example, 1 or 2 halogen atoms; alkylthio, e.g. methylthio, ethylthio, propylthio and n-butylthio; aralkylthio; alkenylthio; cycloalkylthio; cycloalkenylthio; arylthio, e.g. phenylthio; arylcarbonyl, e.g. benzoyl; arylamino and N-alkyl-N-arylamino in which the aryl is e.g. phenyl or phenyl substituted with, for example, one or more halogen atoms; N-alkyl-N-arylsulphonamido; trifluoromethyl; halogen, e.g. fluorine, chlorine and bromine; nitro; alkylamino; dialkylamino; substituted and unsubstituted pyridyl; piperidyl; furyl; morpholino; thiomorpholino, pyrrolinyl, pyrrolidinyl; pyrrolyl; thienyl; or two Q groups together form a carbocyclic or heterocyclic ring, which rings may be aromatic, e.g. naphthyl and substituted naphthyl.

Examples of compounds are those in which the substituent, or one of the substituents, Q is in the 4-position, and is alkyl, e.g. isobutyl, cycloalkyl, e.g. cyclohexyl or cyclohexenyl. Particularly preferred compounds are those in which Ar is

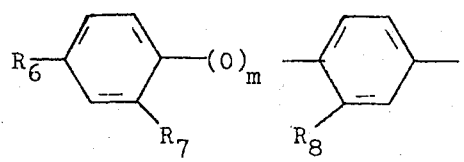

in which $m$ is 0 or 1, and $R_6$, $R_7$ and $R_8$ may be the same or different and are selected from hydrogen, chlorine or fluorine, at least one being chlorine or fluorine, and preferably fluorine. Especially preferred are those compounds in which $m$ is 0.

Examples of such preferred Ar groups are the following:

| m | $R_6$ | $R_7$ | $R_8$ |
|---|---|---|---|
| 0 | H | F | H |
| 0 | H | H | F |
| 0 | H | F | F |
| 0 | F | F | H |
| 0 | F | H | F |
| 0 | F | F | F |
| 0 | F | H | H |
| 1 | F | H | H |
| 1 | F | F | H |
| 1 | H | F | H |
| 1 | F | Cl | H |
| 1 | Cl | H | H |
| 0 | Cl | H | H |
| 0 | Cl | F | F |
| 0 | F | F | Cl |
| 0 | F | Cl | F |

Other suitable Ar groups include 2-(6-methoxynaphthyl) and those in which $n$ is 1 and Q is in the 3 position and is benzoyl or phenoxy.

Preferably the sodium salt of 2-bromopropionic acid is used.

The reaction for producing the compound of formula I is generally carried out in a conventional manner for Grignard reactions, e.g. in an anhydrous aprotic medium, preferably an ether, for example tetrahydrofuran, diethyl ether, 1,2-dimethoxyethane or a mixture of one or more of these. When using the last named this is generally in admixture with another ether. The reaction is generally carried out at a temperature of −20°C to +100°C, preferably −10°C to 70°C, it may suitably be carried out under reflux.

When the acid of formula I is one in which the Ar group contains a functional group which is itself reactive with the Grignard compound e.g. a carbonyl group, it is usually necessary that this functional group be protected before the Grignard compound is formed. The protecting group can then be removed on acidification.

An example of a suitable carbonyl protecting group is a ketal, for example gem-dimethoxy.

If desired the acids may be converted, as is known, to a suitable derivative, e.g. a pharmaceutically acceptable salt or an ester, amide or other pharmaceutically active derivative.

The method of preparation of the 2-bromopropionate salt may affect the yield of the 2-arylpropionic acid. It is usually prepared by reacting 2-bromopropionic acid with a suitable base, e.g. a carbonate or an alkoxide, e.g. a methoxide or t-butoxide. The use of sodium methoxide is particularly preferred.

The invention is illustrated in the following Examples, in which "parts" and "percentages" are by weight, unless otherwise stated.

EXAMPLE 1

A solution of 4-bromo-2-fluorobiphenyl (2.51g;0.01 mole) in dry tetrahydrofuran (15ml) was aded dropwise, with stirring, to magnesium turnings (0.25g;0.0103g. atom) under a nitrogen atomosphere. When the addition was complete, the mixture was stirred and boiled under reflux for 30 minutes. The mixture was then cooled and a suspension of sodium 2-bromopropionate (1.75g;0.01 mole) in dry tetrahydrofuran (20ml) was added. Frothing occurred and when this had subsided the mixture was boiled under reflux with stirring, for one hour. The mixture was then cooled in an ice-bath and water (15ml) was added, followed by sulphuric acid (20%;5ml). The mixture was stirred for 10–15 minutes, and extracted with ether. The extract was washed with water and then extracted with aqueous potassium carbonate (1N). This extract was washed with ether and then added to a mixture of concentrated hydrochloric acid (10ml) and water (20ml). The mixture was cooled overnight and the precipitate filtered, washed with water and dried in vacuo to give 2 -(2-fluoro-4-biphenylyl)propionic acid.

The sodium 2-bromopropionate was prepared by adding methanolic sodium methoxide to a stirred, cooled solution of an equivalent amount of 2-bromopropionic acid in anhydrous methanol (10 molar). The mixture was stirred for a further 15 minutes at room temperature and methanol evaporated under reduced pressure. The residue was finely ground and dried at 55°–60°C. in vacuo.

EXAMPLE 2

Example 1 was repeated except that before addition of the sodium 2-bromopropionate the solution of the Grignard reagent was cooled in an ice bath to 0° to 5°C. and after the addition the mixture was maintained at this temperature and the mixture stirred for one hour instead of being boiled under reflux.

EXAMPLE 3

Example 1 was repeated except that the sodium 2-bromopropionate was prepared by adding anhydrous sodium carbonate, portionwise, to a stirred, cooled solution of an equivalent amount of 2-bromopropionic acid in anhydrous methanol (5 molar). This solution was then stirred for a further 45 minutes at room temperature during which time a further portion of methanol equal to half the original volume was added to prevent crystallisation of the salt. The methanol was then evaporated under reduced pressure, the residue finely ground and dried at 55°–60°C. in vacuo.

EXAMPLE 4

Example 1 was repeated except that the sodium 2-bromopropionate was prepared by adding freshly prepared sodium t-butoxide, portionwise, under nitrogen, to a stirred, cooled solution of an equivalent amount of 2-bromopropionic acid in anhydrous methanol (2.5 molar). This solution was stirred for a further 10 minutes at room temperature and methanol evaporated under reduced pressure. The residue was finely ground and dried at 55°–60°C. in vacuo.

In a similar manner to that described in Example 1, the following compounds were obtained from the appropriate bromo compound. The compounds were purified by recrystallisation from the solvent given in the following table.

TABLE I

| Ex. No. | Compound obtained | Recrystallisation Solvent | M.P. (°C) |
|---|---|---|---|
| 5 | 2-[4-(2-Fluorophenoxy)phenyl]propionic acid | Petroleum (b.p. 60–80°C) | 104–106 |
| 6 | 2(2,2'-Difluoro-4-biphenylyl)propionic acid | '' | 119–121 |
| 7 | 2-(4-Cyclohexylphenyl)propionic acid | '' | 110–111 |
| 8 | 2-(2'-Fluoro-4-biphenylyl)propionic acid | '' | 95–96 |
| 9 | 2-(4-Isobutylphenyl)propionic acid | '' | 72–74 |
| 10 | 2-(2-Fluoro-4'-methoxy-4-biphenylyl)propionic acid | Petroleum (b.p. 80–100°C) | 119–120 |
| 11 | 2-(2,2',4'-Trifluoro-4-biphenylyl)propionic acid | '' | 105–108 |
| 12 | 2-(2-Fluorenyl)propionic acid | '' | 184–186 |
| 13 | 2-(4-Biphenylyl)propionic acid | Methylene Chloride/ Petroleum (b.p. 60–80°C) | 141–143.5 |
| 14 | 2-(6-Methoxy-2-naphthyl)propionic acid | Petroleum (b.p. 100–120°C) | 153–155 |
| 15 | 2-[4-(1-Cyclohexen-1-yl)phenyl]propionic acid | Ether/petroleum (b.p. 40–60°C) | 101–105 |

EXAMPLE 16

In a similar manner to that described in Example 1 using a reaction time of 1 hour the Grignard compound was formed from 3-bromobenzophenone dimethyl ketal and reacted with sodium 2-bromopropionate. The oily product was purified by preparative layer chromatography and the gum resulting was recrystallised from a mixture of benzene and petroleum (b.p. 60°–80°C.) to give 2-(3-benzoylphenyl) propionic acid, m.p. 91°–92°C.

EXAMPLE 17

In a similar manner to that described in Example 1, 2-(3-phenoxyphenyl)propionic acid was obtained as an oil, b.p. 178°–180°C./0.9mm.

EXAMPLES 18 and 19

Examples 14 and 15 were repeated except that the reactions were carried out at 0°–10°C. 2-(6-Methoxy-2-naphthyl) propionic acid, m.p. 153°–155°C. and 2-[4-(1-cyclohexen-1-yl) phenyl]propionic acid, m.p. 105°–107°C. were obtained.

EXAMPLES 20 and 21

Example 1 was repeated using lithium methoxide and magnesium methoxide instead of sodium methoxide and also a reaction time of 1 hour.

EXAMPLES 22 to 24

Example 3 was repeated using lithium carbonate, magnesium carbonate and calcium carbonate instead of sodium carbonate and reaction times of 1½, 2 and ½ hour respectively. The lithium 2-bromopropionate was added dry in a 10% excess to the Grignard compound.

EXAMPLES 25 and 26

Example 1 was repeated but using reaction times of 5 and 30 minutes, respectively.

For the purposes of comparison, reactions similar to those described in Examples 1 to 4 were carried out in which either the Grignard reagent was replaced by the equivalent chloro or iodo compound and/or the sodium 2-bromopropionate was replaced by another salt of a 2-halopropionic acid, the 2-halopropionic acid itself, an ester of a 2-halopropionic acid, or a 2-halopropionamide.

Similar conditions to those of Examples 1 to 4 were used with appropriate modifications depending on the reactants. Thus when the salt of 2-bromopropionic was an amine salt, pre-mixed equimolar amounts of the acid and amine were added to the Grignard reagent. The products from reactions with esters were hydrolysed with aqueous potassium hydroxide in industrial methylated spirits followed by acidification to give the free acid which was recovered by extraction with ether. The products from reactions with amides were hydrolysed with a mixture of acetic acid and sulphuric acid to give the acid which was recovered in a similar manner to that described in Example 1. The results are given in Table II.

The yields given are crude theoretical % yields based on the aryl halide and the melting points and purities (where given) are those of the crude 2-(2-fluoro-4-biphenylyl) propionic acid. The purities were determined by gas-liquid chromatography, and, unless specified, using an internal standard. The same data for the crude products from Examples 1 to 4 and 20 to 26 are also given.

TABLE II

Reaction of 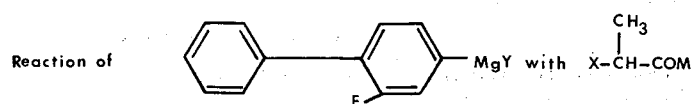

| Ex. No. | X | M | Y | Method of Preparation of Salts | Reaction Temp. (°C) | Reaction Time (hours) | Crude Yield (%) | M.P. (°C) | Purity (%) | Notes |
|---|---|---|---|---|---|---|---|---|---|---|
| 1 | Br | ONa | Br | A | R | 1 | 60.0 | 109–110 | | |
| 2 | Br | ONa | Br | A | 0–5 | 1 | 56.0 | 109–110 | 92.8 | |
| 3 | Br | ONa | Br | B | R | 1 | 52.0 | 110–111 | 91.4 | |
| 4 | Br | ONa | Br | C | R | 1 | 51.0 | 110–112 | 96.3 | |
| 20 | Br | OLi | Br | A | R | 1 | 47.7 | 115–116.5 | | |
| 21 | Br | O(Mg½) | Br | A | R | 1 | 44.8 | 112–113 | | U |
| 22 | Br | OLi | Br | B | R | 1½ | 47.8 | 109–111 | | YZ |
| 23 | Br | O(Mg½) | Br | B | R | 2 | 45.2 | 110–112 | | UWZ |
| 24 | Br | O(Ca½) | Br | B | R | ½ | 41.3 | 110.5–112 | | WZ |
| 25 | Br | ONa | Br | A | R | 5 mins | 61.2 | 110.5–112.5 | 95.2 | |
| 26 | Br | ONa | Br | A | R | ½ | 63.2 | 109–110.5 | | |

| X | M | Y | Method of Preparation of Salts | Reaction Temp. (°C) | Reaction Time (hours) | Crude Yield (%) | M.P. (°C) | Purity (%) | Notes |
|---|---|---|---|---|---|---|---|---|---|
| Br | OK | Br | A | R | 1 | 36.0 | 104–106 | 81.4 | |
| Br | OK | Br | B | R | ½ | 4.8 | 71–74 | 61.5 | |
| Br | OK | Br | C | R | ¾ | 5.8 | 98–100 | 72.6 | |
| Br | OK | Br | A | 0–5 | 1 | 3.1 | 104–107 | 85.6 | |
| Br | OK | Br | B | 0–5 | 1 | 0.9 | 94–95 | 59.1 | |
| Br | OK | Br | C | 0–5 | 1 | Trace | | | |
| I | ONa | Br | A | R | 1 | 32.8 | 108.5–110 | 88.6 | |
| I | ONa | Br | B | R | 1 | 36.3 | 107.5–109 | 89.3 | |
| I | ONa | Br | A | 0–5 | 1 | 32.5 | 108.5–110.5 | 95.0 | |
| I | ONa | Br | B | 0–5 | 1 | 34.3 | 107.5–109.5 | 92.6 | |
| I | OK | Br | A | R | 1 | 32.4 | 108–110 | 89.1 | |
| I | OK | Br | B | R | ½ | 0.8 | 74–76 | 54.7 | |
| I | OK | Br | C | R | 1 | 24.9 | 107–108.5 | 82.8 | |
| I | OK | Br | B | 0–5 | 1 | 0.5 | 82–85 | 67.9 | |
| I | OK | Br | C | 0–5 | 1½ | 15 | 107–108.5 | 93.1 | |
| Cl | ONa | Br | A | R | ½ | Nil | | | |
| Cl | ONa | Br | A | 0–5 | 1 | Trace | | | |
| Cl | OK | Br | A | R | 1 | Nil | | | |
| I | O(Mg)½ | Br | B | R | 2 | 24.1 | | | U |
| Br | O(Zn½) | Br | A | R | 2 | 15.4 | 107–109 | | UWZ |
| Br | O(Cu½) | Br | D | R | 1½ | 6.2 | 102–104 | | WZ |
| Br | O(Ba½) | Br | B | R | ½ | 28.7 | 103–105 | | XZ |
| Br | ONH₄ | Br | E | R | 2 | 4.2 | 107.5–109.5 | | U |
| Br | OH | Br | | R | 2 | 26.0 | 111–112 | | |
| Br | OH | Br | | R | 5 mins | 30.0 | 112–114 | | |
| Br | OH | Br | | –5 | 1½ | Trace | | | |
| I | OH | Br | | R | 1 | 34.0 | 106–108 | | |

TABLE II-continued

Reaction of [biphenyl-F]—MgY with X—CH(CH₃)—COM

| Ex. No. | X | M | Y | Method of Preparation of Salts | Reaction Temp. (°C) | Reaction Time (hours) | Crude Yield (%) | M.P. (°C) | Purity (%) | Notes |
|---|---|---|---|---|---|---|---|---|---|---|
| | I | OH | Br | | 0–5 | 1 | 13.9 | 110–112 | | |
| | Cl | OH | Br | | R | 1 | 1.6 | 103–108 | | |
| | Cl | OH | Br | | 0–5 | 1 | 0.9 | 105–107 | | |
| | Br | ONa | Cl | | R | 1 | 21 | 100–105 | | S |
| | Br | —N⬠ | Br | | R | ½ | 36 | | 96.3 | LTV |
| | Br | —N⬡ | Br | | R | ½ | 35 | | 94.7 | LTV |
| | Br | —N⬡ | Br | | R | ½ | 33 | | 98.6 | LV |
| | Br | —NMe₂ | Br | | R | 1½ | 35.4 | | 94.6 | LVT |
| | Br | ONBu₃H | Br | | R | 1½ | 37.1 | 112–114 | | Z |
| | Cl | ONBu₃H | Br | | R | 1 | 0.4 | 104–106 | | |
| | Cl | ONBu₃H | Br | | 0–5 | 1 | Trace | | | |
| | Br | OpNO₂Ph | Br | | R | 1 | 7 | | | T |
| | Br | OEt | Br | | R | 1 | 5.4 | | | N |
| | Br | OEt | Cl | | R | 1 | <2 | Oil | | |
| | Br | ONa | I | | R | ½ | 4.2 | 88–91 | | |
| | Br | ONa | I | | 0–5 | 1½ | Nil | | | |

Key
A = Metal methoxide + 2-halopropionic acid
B = Metal carbonate + 2-halopropionic acid
C = Metal t-butoxide + 2-halopropionic acid
D = Basic copper carbonate + 2-halopropionic acid
E = Concentrated aqueous ammonia + 2-halopropionic acid
R = Reflux L = 1.3 × molar excess of amide used N = Grignard added to ester
S = Required an equivalent amount of ethyl bromide to initiate Grignard compound formation.
T = Reaction carried out in ether instead of tetrahydrofuran.
U = Salt added in solution
V = Purity determined using GLC normalisation
W = Salt dried at 95°C.
X = Salt dried at 74°C.
Y = Salt dried at 80°C.
Z = Reaction initiated with ethylene dibromide Preparations were also attempted using other amines but in all cases lower yields were obtained than those obtained with amines given in the table. Similarly, further preparations using different esters and amides gave lower yields than obtained with the esters and amides respectively given in the table.

It will be seen that when using a Grignard reagent derived from an aryl bromide and 2-bromopropionate salts according to the invention higher yields of 2-aryl propionic acid are obtained than when using any other combination of reactants. Further, the purity of the crude material is generally higher in those cases where it was determined. The melting points of crude material obtained according to the invention are also generally higher than crude material obtained otherwise, also indicating higher levels of purity. (The melting point of pure 2-(2-fluoro-4-biphenylyl) propionic acid is 113°–114°C.

As a further comparison, Example 12 was repeated in which the sodium 2-bromopropionate was replaced by equivalent amounts of potassium 2-iodopropionate and potassium 2-bromopropionate, both prepared from potassium t-butoxide.

The products from the coupling reactions were subjected to preparative layer chromatography to purify 2-(2-fluorenyl)propionic acid. The details of the products thus obtained are given in Table III. The purities, where determined, were obtained by gas liquid chromatography using a normalisation technique.

TABLE III

| Salt | Reaction Time (hours) | Yield after chromatography (%) | Condition of material | Purity (%) |
|---|---|---|---|---|
| Sodium 2-bromopropionate | 1 | 7.5 | Solid | >85 |
| Potassium 2-iodopropionate | 1 | 3.5 | Oil | 89 |
| Potassium 2-iodopropionate | 20 | 1.1 | Oil | 42 |
| Potassium 2-bromopropionate | 1 | 2.5 | Oil | |

The aryl bromide starting materials whose preparations are not described in the literature or which differ from the literature may be prepared as follows:

4-Bromo-2-fluorobiphenyl

2-Amino-4-bromo-biphenyl was subjected to a Schiemann reaction using hydrofluoroboric acid. The product had a b.p. of 106°–109°C./0.6mm, and a m.p. of 38°–39°C.

4-Bromo-2,2'-difluorobiphenyl

2-Fluoroaniline was diazotized and treated with potassium iodide to give o-fluoroiodobenzene, b.p. 80°–83°C./22mm. This was treated with 2,5-dibromo-1-nitrobenzene under Ullmann conditions to give 4-bromo-2'-fluoro-2-nitrobiphenyl, b.p. 138°–144°C./0.5mm (m.p. 71°–73°C., after recrystallisation from industrial methylated spirits). This was then reduced and subjected to a Schiemann reaction, using hydrofluoroboric acid to give the desired product, b.p. 92°–96°C./0.3mm (m.p. 42°–45°C., after recrystallisation from petroleum (b.p. 40°–60°C.)).

1-Bromo-4-cyclohexylbenzene

1-Bromo-4-(1-cyclohexen-1-yl)benzene was hydrogenated in an ether ethanol solvent containing 50% HBr using a platinum oxide catalyst to give the desired product, b.p. 121–126°C/3 mm.

1-Bromo-4-(2-fluorophenoxybenzene)

2-Fluorophenol and 2,5-dibromo-1-nitrobenzene were reacted together under Ullmann conditions to give 1-bromo-4-(2-fluorophenoxy)-3-nitrobenzene which was reduced and deaminated to give the desired product b.p. 112–116°C./0.8 mm.

1-Bromo-4-isobutylbenzene

A solution of 4-bromophenylmagnesium bromide in ether was treated with isobutyraldehyde to give 1-(4-bromophenyl)-2-methylpropan-1-ol, b.p. 152°–154°C./15mm. This was dehydrated with polyphosphoric acid at 20°C., to give 1-bromo-4-(2-methyl-1-propenyl)benzene, b.p. 110°–112°C./6mm, which was hydrogenated in an ether/ethanol solvent containing 50% hydrobromic acid (2% by volume of solvent) over platinum oxide to give the desired product, b.p. 120°–122°C./22mm.

4-Bromo-2'-fluorobiphenyl 2,5-Dibromo-1-nitrobenzene and o-fluoroiodobenzene were reacted under Ullmann conditions to give 4-bromo2'-fluoro-2-nitrobiphenyl, b.p. 125°–140°C./0.2mm (m.p. 71°–73°C. after recrystallisation from industrial methylated spirits). This was reduced to give 2-amino-4-bromo-2'-fluorobiphenyl, m.p. 52°–54°C., which was deaminated to give the product, b.p. 105°–115°C./0.5mm (m.p. 40°–42°C. after recrystallisation from petroleum, b.p. 40°–60°C.).

4-Bromo-2,2',4'-trifluorobiphenyl 2,5-Dibromo-1-nitrobenzene and 2,4-difluoro-1-iodobenzene were reacted under Ullmann conditions to give 4-bromo-2',4'-difluoro-2-nitrobiphenyl, b.p. 126°–136°C./0.2mm (m.p. 52°–53°C. after recrystallisation from methanol). This was reduced to give 2-amino-4-bromo-2',4'-difluorobiphenyl, b.p. 120°–124°C./0.5mm, which was subjected to a Schiemann reaction, using hydrofluoroboric acid to give the product, m.p. 67°–69°C., after distillation.

4-Bromo-2-fluoro-4'-methoxybiphenyl 2,5-Dibromo-1-nitrobenzene and 4-iodoanisole were reacted under Ullmann conditions to give 4-bromo-4'-methoxy-2-nitrobiphenyl, m.p. 130°–131°C. This was reduced to give 2-amino-4-bromo-4'-methoxybiphenyl, m.p. 128°–130°C., which was subjected to the Schiemann reaction using hydrofluoroboric acid to give the product, b.p. 134°–138°C./0.15mm.

What we claim is:

1. A proces for the preparation of a compound of formula I

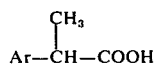

in which Ar is an aryl group which comprises reacting a Grignard compound, obtained from Ar₁Br and magnesium, with a lithium, sodium, magnesium or calcium salt of 2-bromopropionic acid, followed by acidification, and in which Ar₁ is Ar or a group convertible to Ar during the acidification.

2. A process according to claim 1 in which Ar is a substituted phenyl or formula

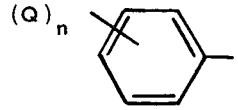

in which $n$ is an integer of 1 to 4 and Q is the same or different and is selected from: alkyl, aralkyl, alkenyl, cycloalkyl, alkyl, substituted cycloalkyl, cyclalkenyl, aryl, alkoxy, aralkoxy, alkenyloxy, cycloalkenyl, cycloalkenyloxy, aryloxy, alkylthio, aralkylthio, alkenylthio, cycloalkylthio, cycloalkenylthio, arylthio, arylcarbonyl, N-alkyl-N-arylamino, arylamino, N-alkylsulphonamido, trifluoromethyl, halogen, nitro, alkylamino, dialkylamino, substituted and unsubstituted pyridyl, piperidyl, furyl, morpholino, thiamorpholino, pyrrolinyl, pyrrolidinyl, pyrrolyl, thienyl, or two Q groups together form a carbocyclic or heterocyclic ring, which rings may be aromatic.

3. A process according to claim 2 in which $n$ is 1 and Q is in the 4-position and is alkyl.

4. A process according to claim 3 in which Q is isobutyl.

5. A process according to claim 2 in which $n$ is 1 and Q is in the 4-position and is cycloalkyl.

6. A process according to claim 5 in which Q is cyclohexyl.

7. A process according to claim 2 in which $n$ is 1 and Q is in the 4-position and is 1-cyclohexen-1-yl.

8. A process according to claim 2 in which Ar is

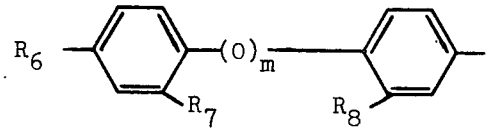

in which $m$ is 0 or 1, and $R_6$, $R_7$ and $R_8$ may be the same or different and are selected from hydrogen, chlorine or fluorine, at least one being chlorine or fluorine.

9. A process according to claim 8 in which $m$ is 0.

10. A process according to claim 9 in which $B_6$ and $R_7$ are hydrogen and $R_8$ is fluorine.

11. A process according to claim 2 in which $n$ is 1 and Q is in the 3-position and is benzoyl.

12. A process according to claim 2 in which $n$ is 1 and Q is in the 3-position and is phenoxy.

13. A process according to claim 2 in which Ar is a substituted 2-naphthyl.

14. A process according to claim 13 in which Ar is 6-methoxy-2-naphthyl.

15. A process according to claim 1 in which the salt of 2-bromopropionic acid is prepared by reacting the acid with a metal alkoxide.

16. A process according to claim 15 in which the alkoxide is the methoxide.

17. A process according to claim 1 in which the salt of 2-bromopropionic acid is the sodium salt.

18. A process according to claim 1 which is carried out in an ethereal medium.

19. A process according to claim 18 in which the ether is selected from tetrahydrofuran, diethyl ether and 1,2-dimethoxyethane and mixtures of two or more of these.

20. A process according to claim 19 in which the ether is tetrahydrofuran.

* * * * *